(12) United States Patent
Poupyrev et al.

(10) Patent No.: US 11,775,050 B2
(45) Date of Patent: Oct. 3, 2023

(54) MOTION PATTERN RECOGNITION USING WEARABLE MOTION SENSORS

(71) Applicant: Google LLC, Mountain View, CA (US)

(72) Inventors: Ivan Poupyrev, Sunnyvale, CA (US); Daniel Kaufman, Redwood City, CA (US)

(73) Assignee: GOOGLE LLC, Mountain Vew, CA (US)

( * ) Notice: Subject to any disclaimer, the term of this patent is extended or adjusted under 35 U.S.C. 154(b) by 356 days.

(21) Appl. No.: 16/487,652

(22) PCT Filed: Jun. 18, 2018

(86) PCT No.: PCT/US2018/037984
§ 371 (c)(1),
(2) Date: Aug. 21, 2019

(87) PCT Pub. No.: WO2018/236702
PCT Pub. Date: Dec. 27, 2018

(65) Prior Publication Data
US 2021/0026440 A1    Jan. 28, 2021

Related U.S. Application Data

(60) Provisional application No. 62/539,187, filed on Jul. 31, 2017, provisional application No. 62/521,866, filed on Jun. 19, 2017.

(51) Int. Cl.
*G06F 3/01* (2006.01)
*A61B 5/11* (2006.01)
(Continued)

(52) U.S. Cl.
CPC .............. *G06F 3/011* (2013.01); *A43B 3/34* (2022.01); *A61B 5/1118* (2013.01); *G06F 1/163* (2013.01); *A61B 2562/0219* (2013.01)

(58) Field of Classification Search
CPC ........ G06F 3/011; G06F 1/163; G06F 3/0484; G06F 3/0346; A43B 3/0005; A61B 5/1118
See application file for complete search history.

(56) References Cited

U.S. PATENT DOCUMENTS

2010/0035688 A1* 2/2010 Picunko ............... A43B 3/0005
463/39
2013/0328763 A1* 12/2013 Latta ....................... G06F 3/017
345/156

(Continued)

OTHER PUBLICATIONS

International Search Report and Written Opinion for PCT/US2018/037984, dated Sep. 17, 2018, 13 pages.
(Continued)

*Primary Examiner* — Matthew A Eason
*Assistant Examiner* — Chayce R Bibbee
(74) *Attorney, Agent, or Firm* — Dority & Manning, P.A.

(57) ABSTRACT

Embodiments of the disclosed technology are directed to classifying motion data collected by wearable sensors. Motion data collected by a first wearable motion sensor and a second wearable motion sensor during the performance of an activity can be obtained. The motion data from the first wearable motion sensor can include data associated with one or more first motion primitives and the second motion data collected by the second wearable motion sensor can include data associated with one or more second motion primitives. The first motion data and the second motion data can be synchronized based at least in part on time stamp information. Data associated with a signature motion classification associated with the activity can be determined based at least in part on the one or more first motion primitives and the one or more second motion primitives.

19 Claims, 6 Drawing Sheets

(51) Int. Cl.
*G06F 1/16* (2006.01)
*A43B 3/34* (2022.01)

(56) References Cited

U.S. PATENT DOCUMENTS

2015/0151160 A1* 6/2015 Balakrishnan ......... G16H 40/67
  700/91
2015/0277557 A1* 10/2015 Raffa ...................... G06F 3/014
  345/156

OTHER PUBLICATIONS

Pirttikangas et al, "Feature Selection and Activity Recognition from Wearable Sensors", Ubiquitous Computing Systems, Oct. 11-13, 2006, Seoul, Korea, pp. 316-327.

* cited by examiner

MOTION PATTERN RECOGNITION USING WEARABLE MOTION SENSORS

PRIORITY CLAIM

The present application is based upon and claims the right of priority under 35 U.S.C. § 371 to International Application No. PCT/US2018/037984, filed on Jun. 18, 2018, which claims the benefit of priority of U.S. Provisional Application Ser. No. 62/539,187, filed on Jul. 31, 2017, and U.S. Provisional Application Ser. No. 62/521,866, filed on Jun. 19, 2017. Applicant claims priority to and the benefit of each of such applications and incorporates all such applications herein by reference in their entirety.

FIELD

The present disclosure relates generally to motion pattern recognition based on data collected from wearable motion sensors.

BACKGROUND

Motion sensors have been integrated into shoes and other wearable apparel for collecting information concerning movement of a user. For instance, motion sensors integrated into athletic shoes have been used to measure speed, acceleration, and other motion of an athlete. Smart shoes have been developed that can include multiple different types of sensors to measure multiple motion parameters relating to physical processes, such as pressure at various points of a shoe, bend of the sole, orientation, acceleration, force, angular motion, translational position, etc. Some smart shoes can communicate with a user device (e.g., via a wireless connection) and can include vibration sensor(s), positioning sensor(s) (e.g., global positioning system technology), and display devices for presenting information to the user.

SUMMARY

Aspects and advantages of embodiments of the present disclosure will be set forth in part in the following description, or may be learned from the description, or may be learned through practice of the embodiments.

One example aspect of the present disclosure is directed to a method for classifying motion data collected by wearable sensors. The method includes obtaining, by one or more computing devices, first motion data collected by a first wearable motion sensor during the performance of an activity. The first motion data includes data associated with one or more first motion primitives. The method includes obtaining, by one or more computing devices, second motion data collected by a second wearable motion sensor during the performance of the activity. The second motion data includes data associated with one or more second motion primitives. The method includes synchronizing, by the one or more computing devices, the first motion data and the second motion data based at least in part on timestamp data associated with the first motion data and the second motion data. The method includes obtaining, by the one or more computing devices, data associated with a classification of a signature motion pattern associated with the activity. The classification of the signature motion pattern is determined based at least in part on the one or more first motion primitives and the one or more second motion primitives.

Other example aspects of the present disclosure are directed to systems, apparatus, tangible, non-transitory computer-readable media, user interfaces, memory devices, and electronic devices associated for motion pattern recognition using wearable sensors.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which.

DETAILED DESCRIPTION

Figure 1:
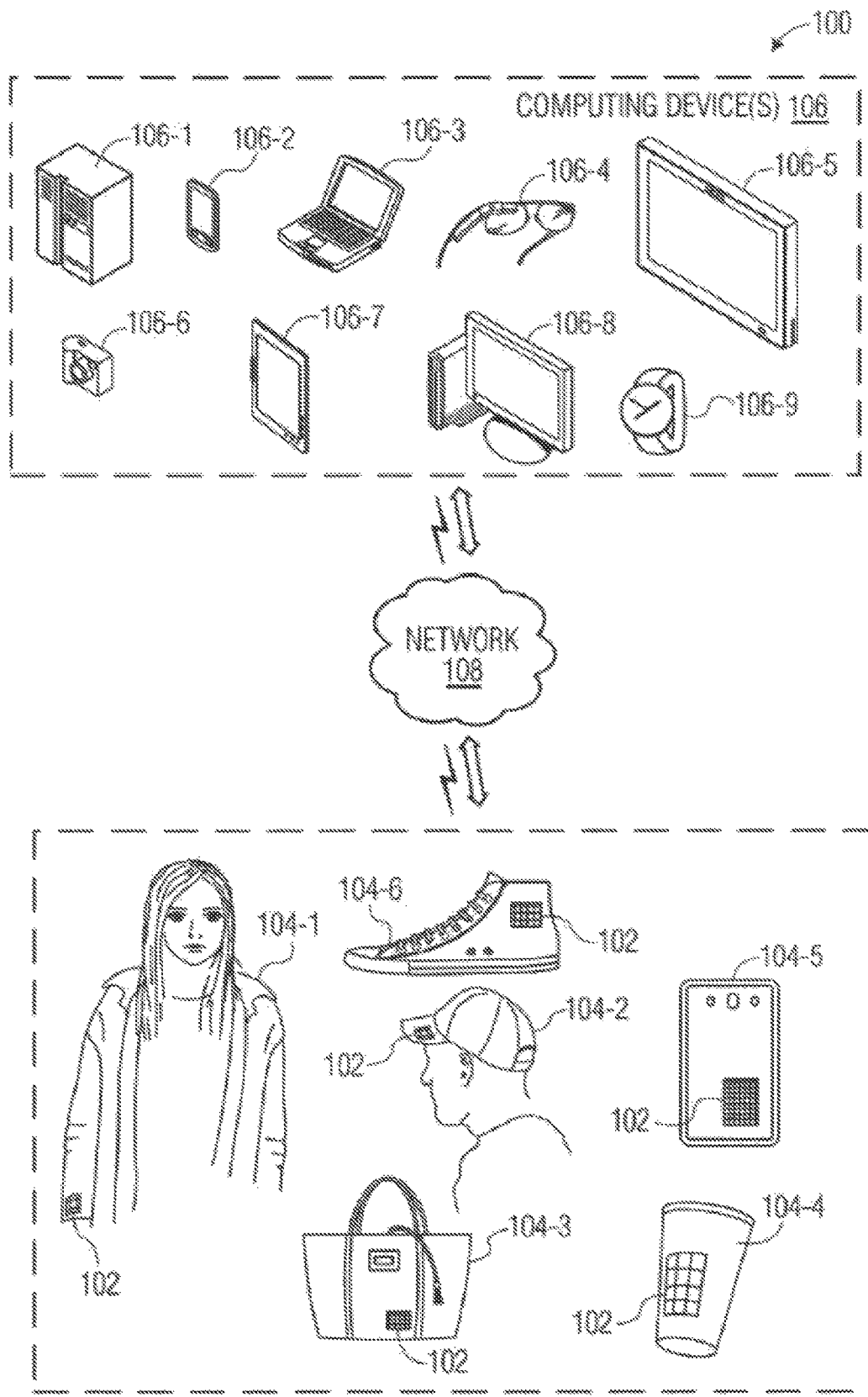
FIG. 1 depicts an example environment including wearable motion sensors according to example embodiments of the present disclosure.

Reference will now be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Example aspects of the disclosed technology are directed to systems and methods for recognizing motion patterns based on data collected by wearable sensors, such as motion sensors (e.g., accelerometers) integrated into shoes, clothing, glasses, wearable patches, or other wearable items. Data collected by wearable sensor(s) worn by a user during movement through a space or performance of an activity (e.g., sport, dance, exercise, work, etc.) can be analyzed to identify particular signature motion patterns of interest. Information associated with the signature motion patterns can be presented to the user as feedback on a user interface presented, for instance, on a display of a user device. The wearable sensors described herein may be physically and permanently coupled to an object, or may be removably coupled to an object. As such, information relating to an underlying physical process may be provided to a user; this can, for example, facilitate greater understanding of underlying physical conditions and additionally or alternatively lead to an ability to improve physical interactions.

As one example, a user can wear a wearable sensor (e.g., accelerometer) in each of the user's shoes. The user can wear the shoes during the performance of an activity, such as a game of basketball, a run, an exercise routine, a golf swing, etc. Motion data collected by the wearable accelerometer sensors can be collected by the sensors during performance of the activity. Once the user completes the activity and/or in real-time as the activity is being performed, the motion data can be communicated from the sensors to a user device (e.g., a smartphone, tablet, laptop, display with one or more processors, etc. and/or a remote server for cloud-based processing, etc.). The motion data can be analyzed (e.g., using machine-learned models) on the user device and/or in a cloud computing system to identify signature motion patterns of interest. Information associated with the signature motion patterns of interest can then be provided to the user. By way of example, information corresponding to a comparison of the motion data with a reference set of motion data can be provided. More particularly, for instance, feedback can be provided to a user in real-time when the motion data deviates from the reference set of motion data (e.g., using one or more thresholds).

A signature motion pattern can be a motion pattern identified to be relevant for a particular activity. For example purposes, the signature motion pattern of interest can include, for instance, motion patterns associated with football tricks and/or performance, basketball performance, runner performance, walking patterns, patterns used to identify neurological abnormalities (e.g., tremors), patterns associated with recovery of injuries, patterns associated with measuring heartbeat through vibration of body, patterns associated with measuring impact on knees, feet, elbows, and other body parts, patterns associated with estimating posture, dance moves, skiing or snowboarding motions or tricks, golf performance, golf swing analysis, tennis performance, work related performance, etc. Aspects of the present disclosure can be used to identify other signature motion patterns of interest without deviating from the scope of the present disclosure.

More particularly, in some examples, multiple wearable sensors can measure and record data associated with movement of a user as the user moves through a space. The wearable sensors can be configured to collect various motion data, such as data indicative of speed, acceleration, velocity, vibration, orientation, and/or other motion data. The wearable motion sensors can include, for instance, one or more accelerometer(s), inertial measurement unit(s), gyroscope(s) (e.g., three-axis gyroscope(s)), vibration sensor(s), piezoelectric sensor(s), altimeter(s), optical sensor(s), and/or other suitable sensors configured to capture data indicative of movement of a user. In some embodiments, data can be collected that represents a state of the user, such as EED or brain waves, ECG, respiration, etc. The wearable sensors can be integrated, included as part of, or attached to one or more a user's shoes, clothing, hats, sporting equipment, watch, wearable patches, etc. In some examples, the wearable sensors may be removed from one garment or other article and subsequently attached or otherwise coupled to another garment or article. The sensor data collected by a sensor may be associated with a particular location or placement of the sensor on a body of a user, a particular garment and/or garment type, and/or a sensor type.

In some embodiments where the systems and method discussed herein collect information about users, the users may be provided with an opportunity to control whether programs or features collect the information and control whether and/or how to receive content from the system or other application. In some embodiments, no such information or data is collected or used until the user has been provided meaningful notice of what information is to be collected and how the information is used. The information is not collected or used unless the user provides consent, which can be revoked or modified by the user at any time. Thus, the user can have control over how information is collected about the user and used by the application or system. In addition, certain information or data can be treated in or more ways before it is stored or used, so that personally identifiable information is removed.

According to example aspects of the present disclosure, each wearable sensor can measure raw motion data during the performance of an activity. The motion data can be processed to determine data indicative of motion primitives as the user performs activities. The data indicative of motion primitives can be stored on the wearable sensor. Motion primitives can be a set of predefined motion parameters that can be indicative of particular signature motion patterns of the user. The motion primitives can be part of a motion primitive vocabulary identified from analysis of motion patterns representative of signature motions of interest, such as motions related to particular sports, walking patterns, posture, exercise movements, etc. In some embodiments, the motion primitives can include motion data such as, peak velocity, average velocity, average acceleration, peak acceleration, vibration parameters, change in direction, etc. In some embodiments, the motion primitives can be classification features identified using machine learning as indicative of particular signature motion patterns.

In some embodiments, the set of motion primitives can depend on the part of the human body that is being measured, due to bio-mechanical constraints of the human body, for example. In other words, as an example, the feet of a human can only move in a certain number of ways and with a certain speed. Therefore, a set of motion primitives can be associated with feet motion. The set of standard motion primitives may be different for measuring motions of the hand or head or torso, for example.

The motion primitives can be determined from raw motion data (e.g., speed data, acceleration data, etc.) collected by the wearable sensors. In some embodiments, the motion primitives are each associated with a time stamp. The motion primitives and time stamps can be continually stored on a memory device included as part of the wearable motion sensor as the user moves through the space and/or performs an activity. Communication (e.g., wireless communication) among wearable motion sensors is not required as the time stamps can be used to sync together motion primitives and motion data collected by a plurality of wearable motion sensors.

Once a user has finished performing an activity, the user can link the wearable sensors to a user device to upload the motion data collected by the wearable sensor to the user device. For instance, the user can connect the wearable motion sensors to a user device (e.g., smartphone, tablet, etc.) via a wired and/or wireless connection. In addition and/or in the alternative, the wearable motion sensors can periodically connect to the user device e.g., at regular intervals and/or irregular intervals) and upload motion data, including the motion primitives from time to time. In addition and/or in the alternative, the wearable motion sensors can maintain a connection to a user device and provide updated motion data in real-time as the data is collected from the sensors.

Time stamps associated with the motion data (e.g., motion primitives) can be used to sync motion data from multiple wearable sensors. The synchronized motion data can be analyzed to identify the signature motion patterns of interest. In some embodiments, the synchronized motion data can be analyzed on the user device to identify the signature motion patterns of interest. In some embodiments, the data can be uploaded to a cloud computing system or other computing system to identify the signature motion patterns of interest.

In some embodiments, the motion patterns can be identified using one or more models developed for particular activities using machine learning (e.g., deep learning). Each model can analyze the motion data (e.g., motion primitives) and classify a particular motion as a signature motion pattern.

In some embodiments, the model(s) can be accessed from a library of models. Each model in the library of models can be associated with a particular activity (e.g., sport, exercise movement, gait analysis, etc.). Each model can also be associated with a particular type of motion sensor and/or motion sensor placement. For instance, a first model in the library of models can be associated with motion sensors located in both of a user's shoes. A second model in the library of models can be associated with motion sensors located in both of a user's shoes and an additional motion sensor located on apparel worn by the user (e.g., a sensor located on a user's shirt near the user's shoulder).

In some embodiments, the motion data collected by the motion sensors can be used to train and/or refine the models in the library of models to improve classification capabilities of the models. For instance, a user can associate truth data with the motion data (e.g., motion primitives) collected by the wearable sensors. The truth data and the motion data can be used to train and/or refine the models using machine learning techniques.

The systems and methods of the present disclosure can be scalable across the entire human body. For instance, in some embodiments, multiple wearable motion sensors can be included on a garment or other item of apparel worn by the user during performance of an activity. As an example, a first wearable sensor can be located on the shoulder of a jacket and a second wearable sensor can be located on a lower back portion of the jacket. These wearable sensors can collect motion data that can be analyzed to identify signature motion patterns associated with tennis, golf, stress injuries, or other activities. As another example, motion sensors can be located on both arms of the jacket to track hand gestures and arm motions during performance of the activity. As yet another example, the motion sensors can be removably-attached to articles so that a sensor can collect data associated with different objects and/or different parts of a user body. For instance, a sensor can be attached at a first garment location and collect sensor data associated with a first part of a user's body during a first activity and then be attached at a second garment location to collect sensor data associated with a second part of the user's body during a second activity.

In some embodiments, the wearable sensors can be moved from one location on the human body to another without requiring modification of the wearable sensor. For instance, a wearable sensor can be moved from a user's shoe to a user's garment. The model used to analyze the motion data and identify signature motion patterns from the data can be selected based on the positioning of the wearable motion sensors. By way of example, a first machine-learned model can be used to analyze motion data collected by a sensor in association with a first location of a user's body and a second machine-learned model can be used to analyze motion data collected by the sensor in association with a second location of the user's body. Machine-learned models may be associated with one or more of a sensor placement, a sensor type, a garment type, a body part or body location, etc.

In some embodiments, user movement data (e.g., the motion data collected by the sensors, the data associated with the motion primitives, and/or data associated with the signature motion patterns) can be used to provide feedback information to a user. For instance, the user movement data can be compared to a reference set of data to provide feedback information to the user concerning performance of a movement or activity. The reference set of data can be associated with, for instance, performance of the movement or activity by a professional athlete, a friend, a competitor, or the user's past performance of the movement or activity. In some embodiments, the reference set of data can be defined as an ideal motion pattern for a particular movement or activity.

Deviations of the user movement data relative to the reference set of data can be used to provide feedback information to the user (e.g., via a graphical user interface or other interface) so that the user can compare performance. The feedback information can be presented in any suitable format to provide information to the user about how performance of a movement or activity compares to the reference set of data.

In some embodiments, a score can be generated based on how closely the movement data tracks the reference set of data. The score can provide an indication of user performance during the activity. The scores can be shared among friends, for instance, in an online community or in other manners to facilitate social interaction around the activity.

As one example, a user can wear the wearable sensors during the performance of an activity, such as a power clean Olympic weightlifting movement. The motion data can be processed to identify data associated with one or more motion primitives and to identify data associated with one or more signature motion patterns according to example aspects of the present disclosure. The data can be compared to a reference set of movement data associated with ideal performance of the power clean. Feedback information associated with deviations from the ideal performance can be provided to the user. For instance, the data can indicate that the user was not in an ideal position for catching the weight during the power clean. The user can then work on technique to ensure the movement is being performed with proper form. The feedback can include instructions to the user for correcting the technique.

In some embodiments, the feedback information can be provided in real time and/or near real time to the user as the user is performing the activity. For instance, the user can wear the wearable sensors during the performance of an activity. The motion data can be processed on the wearable motion sensor and/or uploaded as the user performs the activity to a computing device so that the motion data can be processed to identify data associated with one or more motion primitives and/or one or more signature motion patterns.

The motion data, the data associated with the one or more motion primitives, and/or the data associated with one or more signature motion patterns can be compared to a reference set of data. When the movement data deviates from the reference set of data (e.g., by a threshold) a feedback notification can be provided to the user. The feedback notification can be, for instance, a haptic notification, an audible notification, a visual notification, etc. In some embodiments, the feedback information can include audible instructional information notifying the user that the user is performing a movement the wrong way and providing tips for correcting technique.

Embodiments in accordance with the disclosed technology provide a number of technical effects and benefits, particularly in the areas of motion sensing and computing technology. For instance, techniques are described for identifying motion patterns based on motion data obtained from different wearable motion sensors. More particularly, computer enabled processes for synchronizing motion data received from different wearable motion sensors are provided. In some examples, timestamps are utilized such that remote computing systems can effectively synchronize motion data associated with different wearable motion sensors. In this manner, motion patterns can be detected based on movements detected at multiple body parts and/or locations on a body part. Additionally, motion primitives can be used to identify motion data by a sensor in some examples to reduce bandwidth and processing requirements. For example, motion primitives may be identified by a sensor based on motion data. The motion primitives may be predefined and in some examples, data indicative of the motion primitives may be less than data indicative of raw motion data.

In addition, embodiments of the disclosed technology enable classifications of signature motion patterns to be obtained through the use of classification models specific to particular sensors, locations, or other criteria. Accurate classifications of motion patterns can be obtained where multiple, different types of sensors associated with different user body parts are utilized, for example. Moreover, a sensor can be placed in different locations and motion parameters associated with such placements can be determined without specific modifications or configurations of the sensor. A machine-learned model library may be used and an appropriate model selected for analyzing motion data from a sensor based on the sensor placement. A computing system can access a machine-learned model library and select a particular machine-learned model associated with particular types of motion data. Accordingly, the computing system can accurately determine motion patterns based on classification specific models. In this manner, sensors may be used to collect motion data associated with multiple motion types and/or locations without modification or reconfiguration of the sensors. Additionally, a computing system need not reconfigure sensors for specific motion detections. A computing system can access a machine-learned model associated with a particular sensor placement, etc. to determine motion patterns for different body parts, locations, etc.

FIG. 1 is an illustration of an example environment 100 in which wearable motion sensors can be implemented. Environment 100 includes a wearable motion sensor 102, which is shown as being integrated within various objects 104. Wearable motion sensor 102 can include any suitable sensor for sensing information in association with environment 100.

In environment 100, objects 104 include "flexible" objects, such as a shirt 104-1, a hat 104-2, a handbag 104-3 and a shoe 104-6. Wearable motion sensor 102 may be integrated within any type of flexible object made from fabric or a similar flexible material, such as garments or articles of clothing, garment accessories, garment containers, blankets, or fabric casings, to name just a few. Examples of garment accessories may include sweat-wicking elastic bands to be worn around the head, wrist, or bicep. Other examples of garment accessories may be found in various wrist, arm, shoulder, knee, leg, and hip braces or compression sleeves. Headwear is another example of a garment accessory, e.g. sun visors, caps, and thermal balaclavas. Examples of garment containers may include waist or hip pouches, backpacks, handbags, satchels, hanging garment bags, and totes. Garment containers may be worn or carried by a user, as in the case of a backpack, or may hold their own weight, as in rolling luggage.

In this example, objects 104 further include "hard" objects, such as a plastic cup 104-4 and a hard smart phone casing 104-5. It is to be noted, however, that hard objects 104 may include any type of "hard" or "rigid" object made from non-flexible or semi-flexible materials, such as plastic, metal, aluminum, and so on. For example, hard objects 104 may also include bottles, balls, plastic pads, to name just a few. In another example, hard objects 104 may also include garment accessories such as chest plates, helmets, goggles, shin guards, and elbow guards. Alternatively, a hard or semi-flexible garment accessory may be embodied by a shoe, cleat, boot, or sandal. Wearable motion sensor 102 may be integrated within hard objects 104 using a variety of different manufacturing processes. In one or more implementations, injection molding is used to integrate sensors 102 into hard objects 104. Wearable motion sensor 102 may be integrated within non-flexible or flexible objects 104 in a variety of different ways, including by using fasteners (e.g., clips, etc.), pockets, pouches, containers, weaving, sewing, gluing, and so forth.

Wearable motion sensor 102 enables collected motion data to be used by a variety of other computing devices 106 via a network 108. Computing devices 106 are illustrated with various non-limiting example devices: server 106-1, smart phone 106-2, laptop 106-3, computing spectacles 106-4, television 106-5, camera 106-6, tablet 106-7, desktop 106-8, and smart watch 106-9, though other devices may also be used, such as home automation and control systems, sound or entertainment systems, home appliances, security systems, netbooks, and e-readers. Note that computing device 106 can be wearable (e.g., computing spectacles and smart watches), non-wearable but mobile (e.g., laptops and tablets), or relatively immobile (e.g., desktops and servers).

Network 108 includes one or more of many types of wireless or partly wireless communication networks, such as a local-area-network (LAN), a wireless local-area-network (WLAN), a personal-area-network (PAN), a wide-area-network (WAN), an intranet, the Internet, a peer-to-peer network, point-to-point network, a mesh network, and so forth. Wearable motion sensor 102 can interact with computing devices 106 by transmitting motion data through network 108. Computing device 106 uses the motion data as part of controlling or presenting information using computing device 106 or applications at computing device 106.

Figure 2:
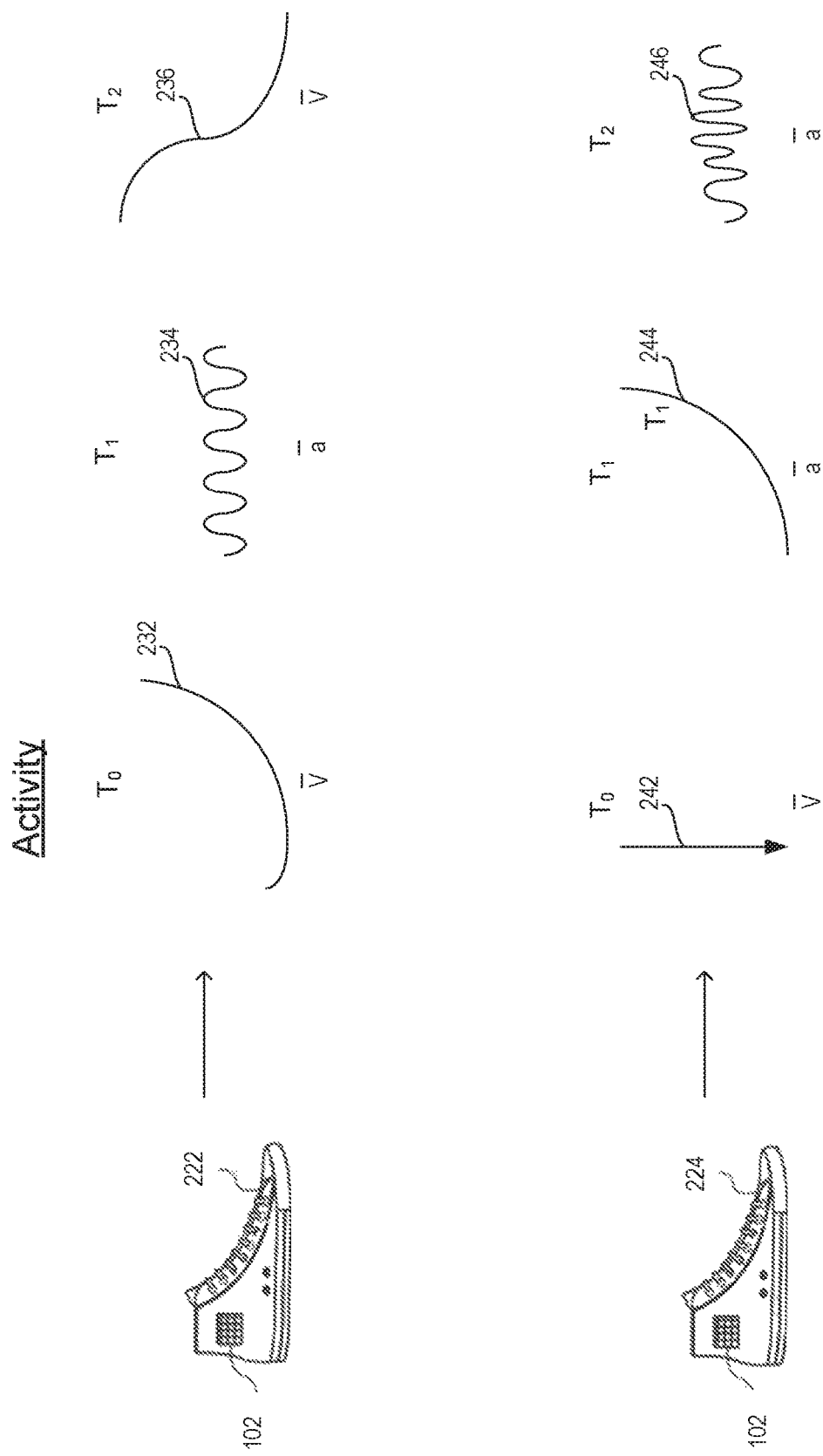
FIG. 2 depicts example wearable motion sensors and motion primitives according to example embodiments of the present disclosure.

FIG. 2 depicts an example including wearable motion sensors 102 included as part of a user's left shoe 222 and right shoe 224. The wearable motion sensors 102 can include, for instance, accelerometer(s), inertial measurement unit(s), gyroscope(s) (e.g., three-axis gyroscope(s)), vibration sensor(s), piezoelectric sensor(s), altimeter(s), optical sensor(s), and/or other suitable sensors configured to capture data indicative of movement of a user. The wearable motion sensors 102 can be configured to collect motion data (e.g., speed, velocity, orientation, acceleration, vibration, etc.) associated with movement of a user during the performance of an activity.

The wearable motion sensors 102 are illustrated as being included as part of a user's shoes in FIG. 2. Those of ordinary skill in the art, using the disclosures provided herein, will understand that the wearable motion sensors can be integrated, included as part of, or attached to one or more of a user's shoes, clothing, hats, apparel, sporting equipment, watch, wearable patches, etc. and/or any other suitable article or object.

According to example aspects of the present disclosure, the wearable motion sensors 202 can collect data associated with motion primitives. Motion primitives can be particular patterns of motion data (e.g., using machine learning) that have been identified to be indicative of particular signature motion patterns associated with the activity. Motion primitives can be based on, for instance, particular patterns of instantaneous velocity, instantaneous acceleration, peak velocity, peak acceleration, average velocity, average acceleration, etc. Each motion primitive can be associated with a time stamp so that the data associated with the motion primitives can be synchronized with data associated with motion primitives identified and/or collected by other wearable sensors.

For example, as shown in FIG. 2, wearable motion sensor 102 associated with the left shoe 222 can collect data associated with motion primitive 232, motion primitive 234, and motion primitive 236. Motion primitive 232 can be a particular pattern of velocity and can be associated with time stamp $T_0$. Motion primitive 234 can be a particular pattern of acceleration associated with time stamp $T_1$. Motion primitive 236 can be a particular pattern of velocity associated with time stamp $T_2$. It is noted that three motion primitives are provided by way of example only, and that any number and type of motion primitives can be generated and collected by a sensor in accordance with embodiments of the disclosed technology.

Wearable motion sensor 102 associated with the right shoe 224 can collect data associated with motion primitive 242, motion primitive 244, and motion primitive 246. Motion primitive 242 can be a particular pattern of velocity and can be associated with time stamp $T_0$. Motion primitive 244 can be a particular pattern of acceleration associated with time stamp $T_1$. Motion primitive 246 can be a particular pattern of acceleration associated with time stamp $T_2$. Again, the number and type of motion primitives collected by wearable motion sensor 102 are provided by way of example only. The machine-learned models in the library can be identified from an analysis of motion patterns representative of signature motions of interest Once the activity is complete, periodically, in real-time, or at other times, the motion data, including data associated with motion primitives 232, 234, 236, 242, 244, and 246 can be provided to a user computing device and/or directly to another computing device (e.g., a cloud computing device). The motion primitives 232, 234, 236, 242, 244, and 246 can be synced with one another using the time stamps. The motion primitives 232, 234, 236, 242, 244, and 246 can be analyzed using classification models (e.g., machine learning models) to identify signature motion patterns associated with the activity. In other examples, other synchronization techniques may be used to synchronize motion primitives associated with different wearable motion sensors.

Figure 3:
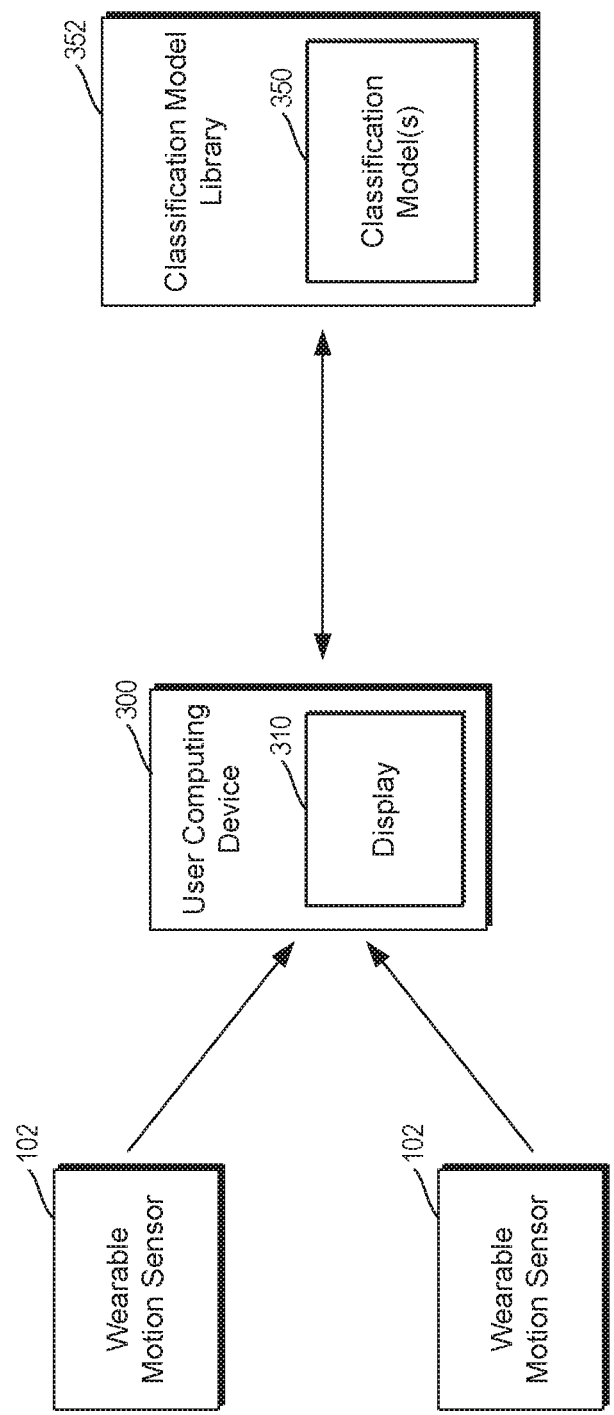
FIG. 3 depicts an example system according to example embodiments of the present disclosure.

More particularly, as shown in FIG. 3, the wearable motion sensors 102 can be connected to or otherwise in communication with a user computing device 300 via a wired and/or wireless connection. Although not shown, the wearable motion sensors 102 can be connected to any other suitable computing device such as computing devices 106 depicted in FIG. 1. The motion data, including data associated with motion primitives 232, 234, 236, 242, 244, and 246 can be uploaded when the wearable motion sensors 102 are connected to the user computing device 300. The user computing device 300 can synchronize the motion data based on time stamps associated with the user computing device 300.

The user computing device 300 can access one or more classification models 350 at a classification model library 352. The classification models 350 can be stored locally on the user computing device 300 and/or can be accessed from other computing systems (e.g., cloud computing systems) in communication with the user device 300. The classification models can be or can otherwise include various machine-learned models such as neural networks (e.g., deep neural networks) or other multi-layer non-linear models. Neural networks can include recurrent neural networks (e.g., long short-term memory recurrent neural networks), feed-forward neural networks, or other forms of neural networks.

The classification model(s) 350 can be used to classify the motion data (e.g., motion primitives) as one or more signature motion patterns associated with the activity. Once classified, information associated with the one or more signature motion patterns can be presented to the user via a user interface, such as a graphical user interface presented on a display device 310 associated with the user computing device 300.

In accordance with some embodiments, the classification models 350 are machine-learned models provided as part of a machine-learned classification model library 352. Each classification model can be associated with a particular activity or activity type, a particular type of motion sensor, a particular motion sensor placement, a particular garment or garment type, and/or particular user body part or other location. The motion data from the sensors can be classified using a particular classification model selected from the library. A particular classification model can be selected based at least in part on the activity or activity type, type of motion sensor, motion sensor placement, garment or garment type, and/or user body part or other location. Synchronized motion data can be input to a selected machine-learned model. The machine-learned model can provide one or more outputs including data associated with a classification of a signature motion pattern based on the synchronized motion data.

Figure 4:
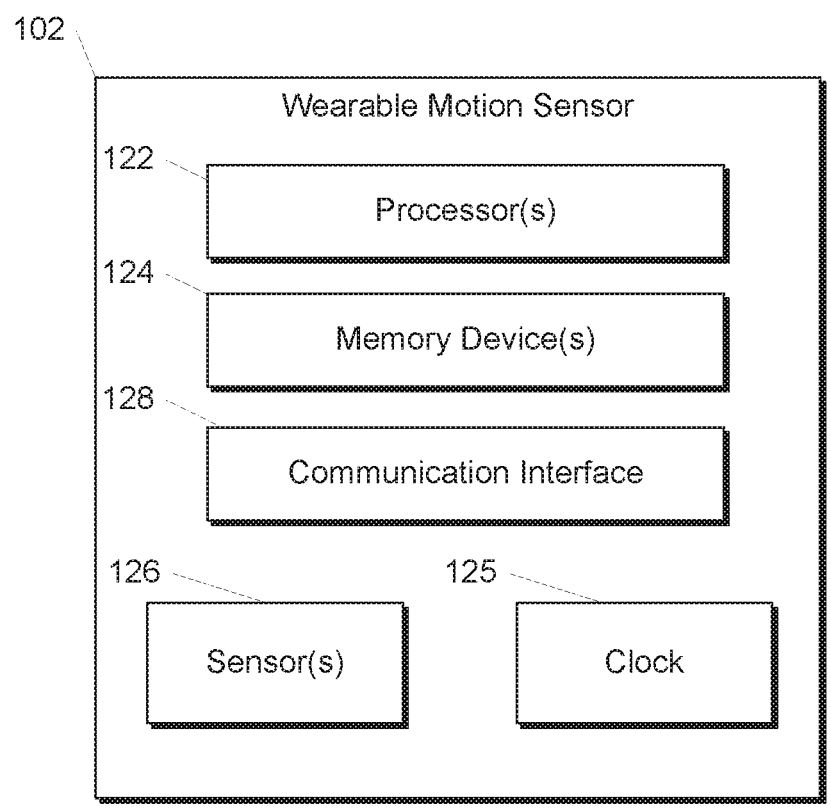
FIG. 4 depicts a block diagram of an example wearable motion sensor according to example embodiments of the present disclosure.

FIG. 4 depicts a block diagram of an example wearable motion sensor 102 according to example embodiments of the present disclosure. The wearable motion sensor 102 can include one or more processors 122 and one or more memory devices 124. The motion sensor 102 can further include one or more sensors 126 configured to acquire motion data to store in the one or more memory devices 124. The one or more sensors 126 can include, for instance, accelerometer(s), inertial measurement unit(s), gyroscope(s) (e.g., three-axis gyroscope(s)), vibration sensor(s), piezoelectric sensor(s), altimeter(s), optical sensor(s), and/or other suitable sensors.

The wearable motion sensor 102 can include a clock 125 configured to associate a time stamp with motion data collected by the sensor(s) 126. The wearable motion sensor 120 can include a communication interface 128. The communication interface 128 can be configured to exchange data with, for instance, a user device, over a wired or wireless connection using any suitable protocol. The communication interface 128 can include, for instance, for example, one or more transmitters, receivers, ports, controllers, antennas, and/or other suitable components. A power supply (e.g., a battery power supply) can provide power to the various components of the wearable motion sensor 120.

Figure 5:
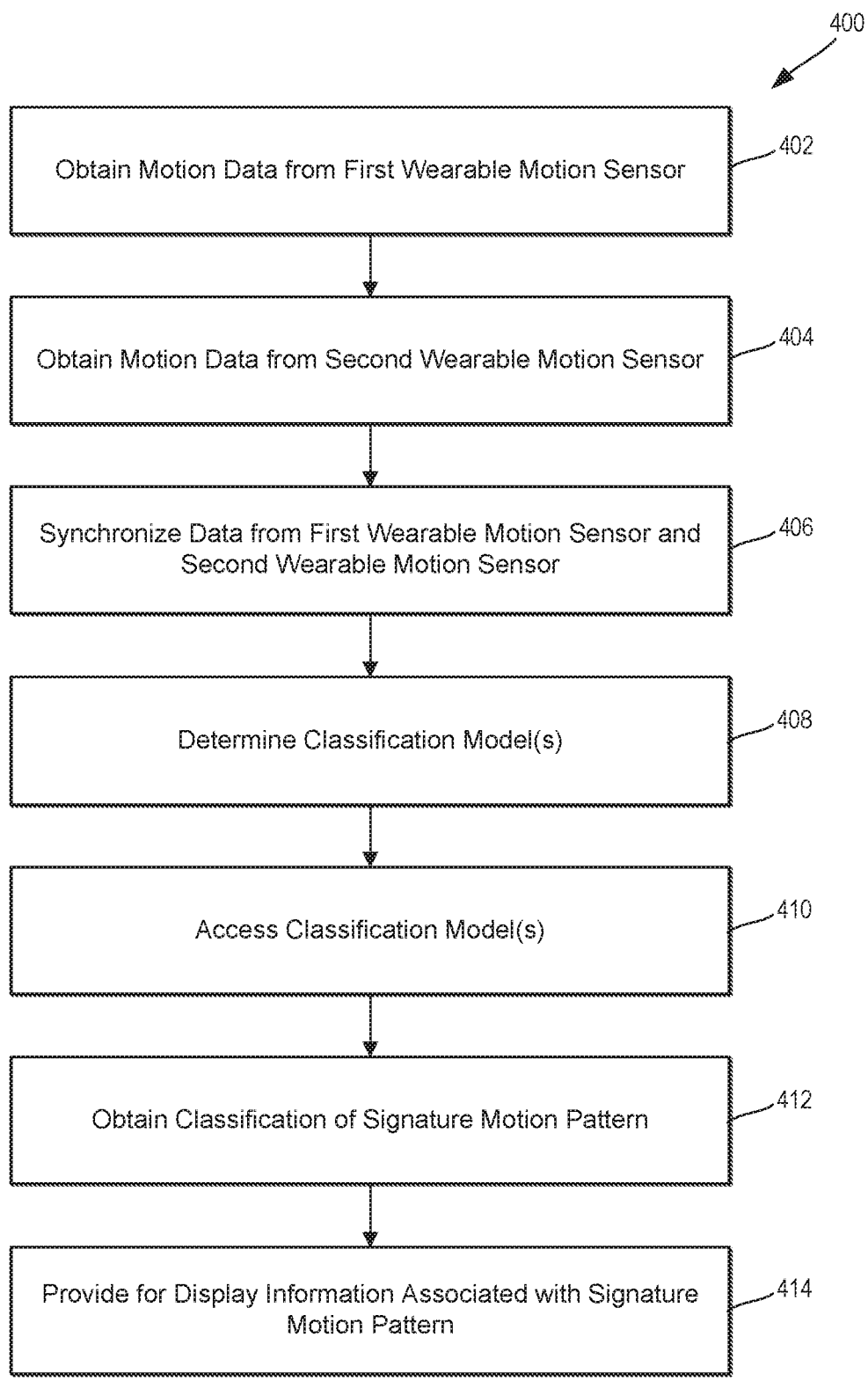
FIG. 5 depicts a flow diagram of an example method according to example embodiments of the present disclosure.

FIG. 5 depicts a flow diagram of an example method (400) according to example embodiments of the present disclosure. The method (400) can be implemented, for instance, by user computing device 300 or other suitable computing device(s). FIG. 5 depicts steps performed in a particular order for purposes of illustration and discussion. Those of ordinary skill in the art, using the disclosures provided herein, will understand that various steps of any of the methods disclosed herein can be omitted, rearranged, performed simultaneously, expanded, and/or modified in various ways without deviating from the scope of the present disclosure.

At (402), the method can include obtaining motion data from a first wearable motion sensor. The first wearable motion sensor can be located in a user's shoe, item of apparel, sporting equipment, or other location on or otherwise associated with a human body. The motion data can be collected during the performance of an activity. As discussed above, the motion data can include data associated with one or more first motion primitives.

At (404), the method can include obtaining motion data from a second wearable motion sensor. The second wearable motion sensor can be located in a user's shoe, item of apparel, sporting equipment, or other location on the human body. The motion data can be collected during the performance of an activity. As discussed above, the motion data can include data associated with one or more second motion primitives. Motion data can be obtained from additional motion sensor(s) without deviating from the scope of the present disclosure.

At (406), the method can include synchronizing motion data from the first wearable motion sensor and the second wearable motion sensor. For instance, time stamps associated with the motion data (e.g., the motion primitives) can be used to synchronize the motion data from the first wearable motion sensor and the second wearable motion sensor.

At (408), the method can include determining one or more classification model(s) to be used to classify the motion data as a signature motion pattern according to example embodiments of the present disclosure. As discussed above, a library of classification models can be available to classify motion data. Parameters associated with the wearable motion sensors and/or data associated with the type of activity during which the motion data was collected can be used to identify the appropriate model(s) to classify the motion data as a signature motion pattern.

For instance, in some embodiments, the locations of the first and second wearable motion sensors (e.g., the user's shoes) can be used to determine an appropriate classification model for classifying the motion data as a signature motion patter. In some embodiments, the type of activity (e.g., sport, exercise movement, analysis of gait, posture analysis, etc.) can be used to determine an appropriate classification for classifying the motion data. Other factors can be used to determine a classification model(s) without deviating from the scope of the present disclosure.

At (410), the classification model(s) can be accessed. The classification model(s) can be accessed from a local memory or can be accessed from a computing system that is located remotely from the user device over a network (e.g., a cloud computing system). The classification models can be or can otherwise include various machine-learned models such as neural networks (e.g., deep neural networks) or other multi-layer non-linear models. Neural networks can include recurrent neural networks (e.g., long short-term memory recurrent neural networks), feed-forward neural networks, or other forms of neural networks.

At (412), the method can include obtaining classification of a signature motion pattern. For example, if a particular set of motion data (e.g., set of motion primitives) is classified as a signature motion pattern (e.g., a particular football trick) using the classification model(s), data associated with the signature motion pattern can be received and/or accessed at the user device.

At (414), the method can include providing for display information associated with the signature motion pattern on a display device, such as part of a graphical user interface presented on the display device. For instance, various metrics (e.g., timing, duration, and other relevant parameters) can be presented as information associated with the signature motion pattern on the display device. Information associated with the signature motion pattern can be presented to the user in other manners without deviating from the scope of the present disclosure. In some examples, at least one output can be provided based at least in part on an identified signature motion pattern. By way of example, a user interface can be used to provide information associated with at least one signature motion pattern. In some examples, the information can include data indicative of a comparison of synchronized motion data relative to one or more reference sets of motion data. The output can include a visual response, an audible response, and/or a haptic response.

As earlier noted, wearable motion sensors may be removably attached to objects so that they can be used to collect motion data in association with different user body parts or locations for instance. As a specific example, a first wearable motion sensor can collect first motion data during performance of a first activity. The first motion data can be associated with a first location of a user's body and include data associated with one or more first motion primitives. The first motion data can be alternately or alternatively associated with a particular garment or other location relative to a user's body. A second wearable motion sensor can collect second motion data during performance of the first activity. The second motion data can be associated with a second location of a user's body and include data associated with one or more second motion primitives. A first classification of a first signature motion pattern can be determined based on the first motion data and the second motion data. By way of example, a first machine-learned model may be used to generate the first classification. The first machine-learned model may be associated with the first location for example.

Subsequent to obtaining the first motion data, third motion data collected by the first wearable motion sensor can be collected. The third motion data can be collected during performance of a second activity. The third motion data can be associated with a third location on the user's body and may include data associated with one or more third motion primitives. A second classification of a second signature motion pattern can be determined based at least in part on the third motion data. By way of example, a second machine-learned model may be used to generate the second classification. The second machine-learned model may be associated with the third location for example.

Figure 6:
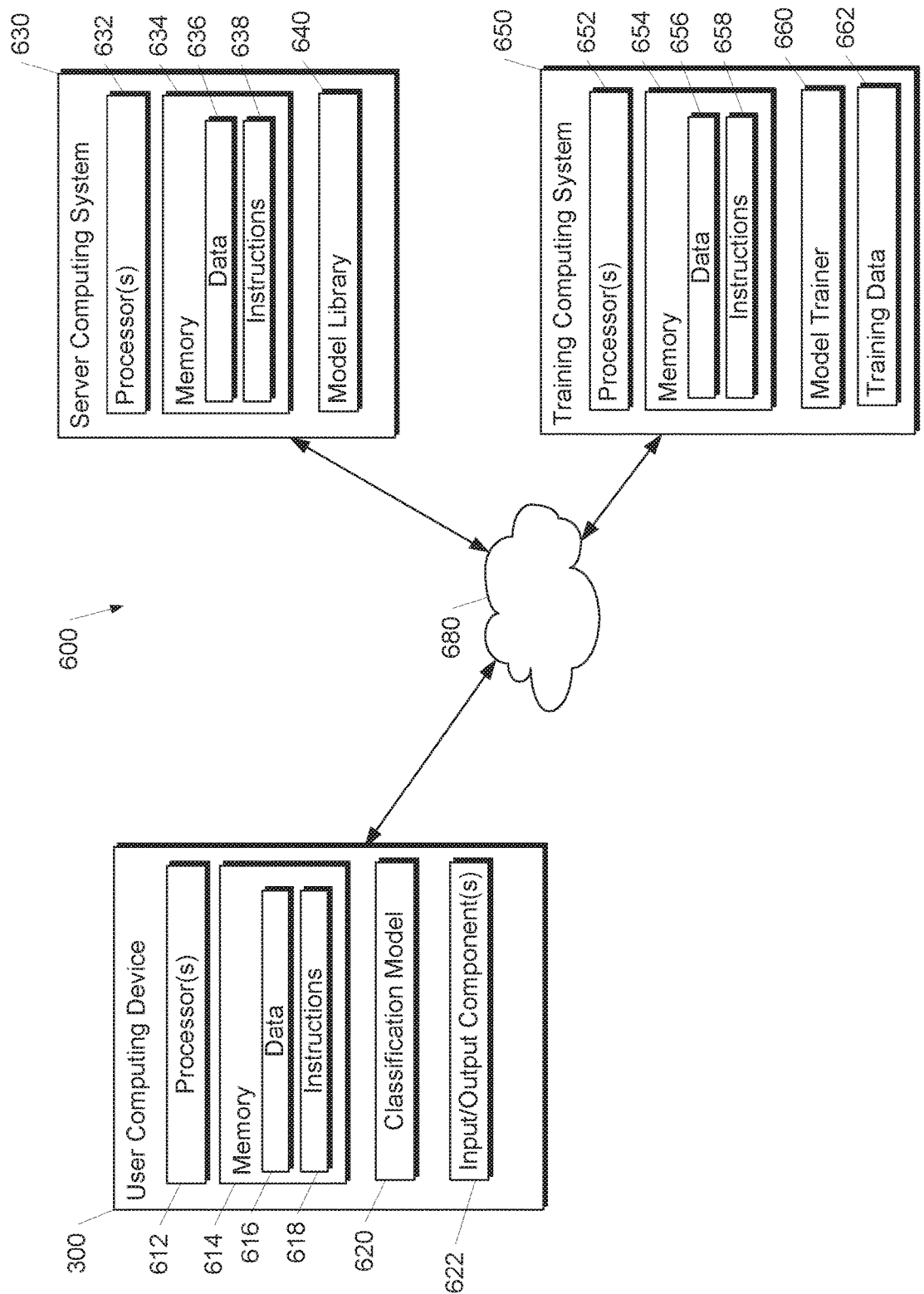
FIG. 6 depicts an example computing system that can be used to implement one or more aspects of example embodiments of the present disclosure.

FIG. 6 depicts an example computing system that can implement one or more aspects of any of the embodiments disclosed herein, including wearable motion sensor 102, computing device(s) 106, and user computing device 300. The system 600 includes one or more of a user computing device 300, a server computing system 630, and a training computing system 650 that are communicatively coupled over a network 680. The system can be implemented using other suitable architectures (e.g., a single computing device) without deviating from the scope of the present disclosure.

The user computing device 300 can be any type of computing device, such as, for example, a personal computing device (e.g., laptop or desktop), a mobile computing device (e.g., smartphone or tablet), a gaming console or controller, a wearable computing device, an embedded computing device, a display with one or more processors, or any other type of computing device.

The user computing device 300 includes one or more processors 612 and a memory 614. The one or more processors 612 can be any suitable processing device (e.g., a processor core, a microprocessor, an ASIC, a FPGA, a controller, a microcontroller, etc.) and can be one processor or a plurality of processors that are operatively connected. The memory 614 can include one or more non-transitory computer-readable storage mediums, such as RAM, ROM, EEPROM, EPROM, flash memory devices, magnetic disks, etc., and combinations thereof. The memory 614 can store data 616 and instructions 618 which are executed by the processor 612 to cause the user computing device 300 to perform operations, such as one or more of the methods described herein.

The user computing device 300 can store, include, or have access to one or more classification models 620 used to classify motion data as a signature motion pattern. For example, the classification models 620 can be or can otherwise include various machine-learned models such as neural networks (e.g., deep neural networks) or other multi-layer non-linear models. Neural networks can include recurrent neural networks (e.g., long short-term memory recurrent neural networks), feed-forward neural networks, or other forms of neural networks.

In some implementations, the one or more classification models 620 can be received or accessed from the server computing system 630 over network 680, stored in the user computing device memory 614, and be used or otherwise implemented by the one or more processors 612 (e.g., via an API). In some implementations, the user computing device 300 can implement multiple parallel instances of a single classification model 620.

Additionally or alternatively, one or more classification models 640 can be included in or otherwise stored and implemented by the server computing system 630 that communicates with the user computing device 300 according to a client-server relationship. For example, the classification models 640 in a model library can be implemented by the server computing system 640 as a portion of a service. Thus, one or more models 620 can be stored and implemented at the user computing device 300 and/or one or more models 640 can be stored and implemented at the server computing system 630.

The user computing device 300 can also include one or more user input component 622 that receives user input. For example, the user input component 622 can be a touch-sensitive component (e.g., a touch-sensitive display screen or a touch pad) that is sensitive to the touch of a user input object (e.g., a finger or a stylus). The touch-sensitive component can serve to implement a virtual keyboard. Other example user input components include a microphone, a traditional keyboard, or other means by which a user can enter a communication.

The server computing system 630 includes one or more processors 632 and a memory 634. The one or more processors 632 can be any suitable processing device (e.g., a processor core, a microprocessor, an ASIC, a FPGA, a controller, a microcontroller, etc.) and can be one processor or a plurality of processors that are operatively connected. The memory 634 can include one or more non-transitory computer-readable storage mediums, such as RAM, ROM, EEPROM, EPROM, flash memory devices, magnetic disks, etc., and combinations thereof. The memory 634 can store data 636 and instructions 638 which are executed by the processor 632 to cause the server computing system 630 to perform operations.

In some implementations, the server computing system 630 includes or is otherwise implemented by one or more server computing devices. In instances in which the server computing system 630 includes plural server computing devices, such server computing devices can operate according to sequential computing architectures, parallel computing architectures, or some combination thereof.

As described above, the server computing system 630 can store or otherwise includes one or more machine-learned classification models 640. For example, the classification models 640 can be or can otherwise include various machine-learned models such as neural networks (e.g., deep recurrent neural networks) or other multi-layer non-linear models.

The server computing system 630 can train the classification models 640 via interaction with the training computing system 650 that is communicatively coupled over the network 680. The training computing system 650 can be separate from the server computing system 630 or can be a portion of the server computing system 630.

The training computing system 650 can include one or more processors 652 and a memory 654. The one or more processors 652 can be any suitable processing device (e.g., a processor core, a microprocessor, an ASIC, a FPGA, a controller, a microcontroller, etc.) and can be one processor or a plurality of processors that are operatively connected. The memory 654 can include one or more non-transitory computer-readable storage mediums, such as RAM, ROM, EEPROM, EPROM, flash memory devices, magnetic disks, etc., and combinations thereof. The memory 654 can store data 656 and instructions 658 which are executed by the processor 652 to cause the training computing system 650 to perform operations. In some implementations, the training computing system 650 includes or is otherwise implemented by one or more server computing devices.

The training computing system 650 can include a model trainer 660 that trains the machine-learned classification models 640 stored at the server computing system 630 using various training or learning techniques, such as, for example, backwards propagation of errors. In some implementations, performing backwards propagation of errors can include performing truncated backpropagation through time. The model trainer 660 can perform a number of generalization techniques (e.g., weight decays, dropouts, etc.) to improve the generalization capability of the models being trained.

In particular, the model trainer 660 can train a classification model 640 based on a set of training data 642. The training data 642 can include, for example, motion data (e.g., data associated with motion primitives) obtained using wearable sensors.

In some implementations, if the user has provided consent, the training examples can be provided by the user computing device 300 (e.g., based on communications previously provided by the user of the user computing device 300). Thus, in such implementations, the model 620 provided to the user computing device 300 can be trained by the training computing system 650 on user-specific communication data received from the user computing device 300. In some instances, this process can be referred to as personalizing the model.

The model trainer 660 includes computer logic utilized to provide desired functionality. The model trainer 660 can be implemented in hardware, firmware, and/or software controlling a general purpose processor. For example, in some implementations, the model trainer 660 includes program files stored on a storage device, loaded into a memory and executed by one or more processors. In other implementations, the model trainer 660 includes one or more sets of computer-executable instructions that are stored in a tangible computer-readable storage medium such as RAM hard disk or optical or magnetic media.

The network 680 can be any type of communications network, such as a local area network (e.g., intranet), wide area network (e.g., Internet), or some combination thereof and can include any number of wired or wireless links. In general, communication over the network 180 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

The technology discussed herein makes reference to servers, databases, software applications, and other computer-based systems, as well as actions taken and information sent to and from such systems. One of ordinary skill in the art will recognize that the inherent flexibility of computer-based systems allows for a great variety of possible configurations, combinations, and divisions of tasks and functionality between and among components. For instance, server processes discussed herein may be implemented using a single server or multiple servers working in combination. Databases and applications may be implemented on a single system or distributed across multiple systems. Distributed components may operate sequentially or in parallel.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A computer-implemented method of classifying motion data associated with wearable sensors, comprising:
    obtaining, by one or more computing devices, first motion data collected by a first wearable motion sensor during performance of an activity, the first motion data including data associated with one or more first motion primitives comprising classification features identified using machine learning at the first wearable motion sensor;
    obtaining, by the one or more computing devices, second motion data collected by a second wearable motion sensor during the performance of the activity, the second motion data including data associated with one or more second motion primitives comprising classification features identified using machine learning at the second wearable motion sensor;
    synchronizing, by the one or more computing devices, the first motion data and the second motion data based at least in part on timestamp data associated with the first motion data and the second motion data; and
    obtaining, by the one or more computing devices, data associated with a classification of a signature motion pattern associated with the activity, wherein the classification of the signature motion pattern is determined using machine learning at the one or more computing devices and is based at least in part on the one or more first motion primitives and the one or more second motion primitives.

2. The computer-implemented method of claim 1, further comprising:
    providing, at a user interface associated with the one or more computing devices, feedback to a user based on the classification of the signature motion pattern.

3. The computer-implemented method of claim 1, further comprising:
    inputting synchronized motion data into one or more machine-learned models configured to identify signature motion patterns, the synchronized motion data is based on synchronizing the first motion data and the second motion data;
    wherein obtaining data associated with the classification of the signature motion pattern comprises obtaining the data associated with the classification from the one or more machine-learned models.

4. The computer-implemented method of claim 3, wherein:
    each of the one or more machine-learned models is associated with a particular activity.

5. The computer-implemented method of claim 3, wherein:
    each of the one or more machine-learned models is associated with a particular type of motion sensor.

6. The computer-implemented method of claim 3, wherein:
    each of the one or more machine-learned models is associated with a particular motion sensor placement.

7. The computer-implemented method of claim 1, wherein:
    the first motion data is collected during performance of a first activity and is associated with a first location on a user body;
    the second motion data is collected during performance of the first activity and is associated with a second location on the user body;
    the classification of the signature motion pattern is a first classification of a first signature motion pattern; and
    the method further comprises:
        obtaining third motion data collected by the first wearable motion sensor during performance of a second activity, the third motion data being associated with a third location on the user body and including data associated with one or more third motion primitives; and
        obtaining data associated with a second classification of a second signature motion pattern associated with the second activity, the second classification of the second signature motion pattern being determined based at least in part on the one or more third motion primitives.

8. The computer-implemented method of claim 7, wherein:
    obtaining data associated with the first classification of the first signature motion pattern comprises obtaining the data associated with the first classification from a first machine-learned model associated with the first location on the user body; and obtaining data associated with the second classification of the second signature motion pattern comprises obtaining the data associated with the second classification from a second machine-learned model associated with the second location on the user body.

9. The computer-implemented method of claim 1, wherein:
the one or more first motion primitives comprise a set of predefined motion parameters.

10. The computer-implemented method of claim 1, wherein:
the data associated with one or more first motion primitives is identified based at least in part on an analysis of motion patterns representative of signature motions of interest.

11. One or more tangible, non-transitory, computer-readable media that store computer-executable instructions that when executed by one or more processors cause the one or more processors to perform operations, the operations comprising:
obtaining first motion data associated with a first wearable motion sensor and second motion data associated with a second wearable motion sensor, the first motion data including data associated with one or more first motion primitives comprising classification features identified using machine learning at the first wearable motion sensor and corresponding to a first sensor placement relative to a user body, the second motion data including data associated with one or more second motion primitives comprising classification features identified using machine learning at the second wearable motion sensor and corresponding to a second sensor placement relative to the user body;
synchronizing the first motion data and the second motion data based at least in part on one or more times associated with the first motion data and the second motion data;
determining at least one signature motion pattern using machine learning and based at least in part on the first motion data and the second motion data; and
providing at least one output based at least in part on the at least one signature motion pattern.

12. The one or more tangible, non-transitory, computer-readable media of claim 11, wherein:
determining the at least one signature motion pattern comprises obtaining from a machine-learned model data indicative of a classification of a first signature motion pattern, the classification of the first signature motion pattern determined based at least in part on the one or more first motion primitives and the one or more second motion primitives.

13. The one or more tangible, non-transitory, computer-readable media of claim 12, wherein:
the machine-learned model is included in a library of machine-learned models; and
each machine-learned model is associated with a particular activity.

14. The one or more tangible, non-transitory, computer-readable media of claim 13, wherein:
each machine-learned model is associated with at least one of a motion sensor type or a motion sensor placement.

15. The one or more tangible, non-transitory, computer-readable media of claim 14, wherein the operations further comprise:
training the one or more machine-learned models using the first motion data and the second motion data.

16. The one or more tangible, non-transitory, computer-readable media of claim 11, wherein:
providing the at least one output comprises providing, at a user interface of one or more computing devices, information associated with the at least one signature motion pattern.

17. The one or more tangible, non-transitory, computer-readable media of claim 16, wherein:
providing information associated with the at least one signature motion pattern comprises providing data indicative of a comparison of the first motion data and the second motion data relative to one or more reference sets of motion data.

18. The one or more tangible, non-transitory, computer-readable media of claim 16, wherein providing information associated with the at least one signature motion pattern comprises:
providing, at the user interface, at least one of a visual response, an audible response, or a haptic response.

19. A computing system for classifying motion data associated with wearable sensors, comprising:
one or more processors; and
one or more tangible, non-transitory, computer-readable media that store one or more machine-learned models configured to generate classifications of signature motion patterns based on motion data from a plurality of sensors, the one or more tangible, non-transitory, computer-readable media store instructions that when executed by the one or more processors cause the computing system to perform operations, the operations comprising:
obtaining first motion data collected by a first wearable motion sensor during performance of an activity, the first motion data including data associated with one or more first motion primitives comprising classification features identified using machine learning at the first wearable motion sensor;
obtaining second motion data collected by a second wearable motion sensor during the performance of the activity, the second motion data including data associated with one or more second motion primitives comprising classification features identified using machine learning at the second wearable motion sensor;
synchronizing the first motion data and the second motion data based at least in part on timestamp data associated with the first motion data and the second motion data; and
obtaining from the machine-learned model data associated with a classification of a signature motion pattern associated with the activity, wherein the classification of the signature motion pattern is determined using machine learning at the one or more computing devices and is based at least in part on the one or more first motion primitives and the one or more second motion primitives.

* * * * *